United States Patent
Bennett

(10) Patent No.: US 10,342,659 B2
(45) Date of Patent: Jul. 9, 2019

(54) PROSTHETIC HEART VALVE WITH RETENTION ELEMENTS

(71) Applicant: W. L. Gore & Associates, Inc., Newark, DE (US)

(72) Inventor: Nathan L. Bennett, Flagstaff, AZ (US)

(73) Assignee: W. L. Gore & Associates, Inc., Newark, DE (US)

(*) Notice: Subject to any disclaimer, the term of this patent is extended or adjusted under 35 U.S.C. 154(b) by 0 days.

(21) Appl. No.: 15/791,562

(22) Filed: Oct. 24, 2017

(65) Prior Publication Data
US 2018/0049872 A1 Feb. 22, 2018

Related U.S. Application Data

(63) Continuation of application No. 14/853,654, filed on Sep. 14, 2015, now Pat. No. 9,827,094.

(60) Provisional application No. 62/050,628, filed on Sep. 15, 2014.

(51) Int. Cl.
*A61F 2/24* (2006.01)

(52) U.S. Cl.
CPC .......... *A61F 2/2418* (2013.01); *A61F 2/2412* (2013.01); *A61F 2/2415* (2013.01); *A61F 2220/0075* (2013.01); *A61F 2230/0054* (2013.01)

(58) Field of Classification Search
CPC ........ A61F 2/24; A61F 2/2418; A61F 2/2415; A61F 2/2412
See application file for complete search history.

(56) References Cited

U.S. PATENT DOCUMENTS

| | | | |
|---|---|---|---|
| 654,799 | A | 7/1900 | Levett |
| 3,953,566 | A | 4/1976 | Gore |
| 4,222,126 | A | 9/1980 | Boretos |
| 4,626,255 | A | 12/1986 | Reichart et al. |
| 4,759,759 | A | 7/1988 | Walker et al. |
| 4,851,000 | A | 7/1989 | Gupta |
| 5,708,044 | A | 1/1998 | Branca |
| 5,928,281 | A | 7/1999 | Huynh |
| 5,944,654 | A | 8/1999 | Crawford |
| 6,086,612 | A | 7/2000 | Jansen |
| 6,129,758 | A | 10/2000 | Love |
| 6,174,331 | B1 | 1/2001 | Moe et al. |
| 6,283,994 | B1 | 9/2001 | Moe et al. |
| 6,541,589 | B1 | 4/2003 | Baillie |
| 6,562,069 | B2 | 5/2003 | Cai |
| 6,755,857 | B2 | 6/2004 | Peterson |
| 6,953,332 | B1 | 10/2005 | Kurk |

(Continued)

FOREIGN PATENT DOCUMENTS

| EP | 1318775 A1 | 6/2003 |
|---|---|---|
| GB | 2513194 A | 10/2014 |

(Continued)

OTHER PUBLICATIONS

International Search Report and Written Opinion from PCT/US2018/053278, dated Dec. 19, 2018, 12 pages.

(Continued)

*Primary Examiner* — Jason-Dennis N Stewart

(57) ABSTRACT

Described embodiments are directed toward centrally-opening leaflet prosthetic valve devices having a leaflet frame and a leaflet construct. The leaflet construct is at least partially coupled to a leaflet frame outer side of the leaflet frame and being coupled thereto by a retention element.

11 Claims, 8 Drawing Sheets

(56) References Cited

U.S. PATENT DOCUMENTS

| | | |
|---|---|---|
| 7,238,200 B2 | 7/2007 | Lee |
| 7,306,729 B2 | 12/2007 | Bacino et al. |
| 7,462,675 B2 | 12/2008 | Chang et al. |
| 7,510,575 B2 | 3/2009 | Spenser et al. |
| 7,531,611 B2 | 5/2009 | Sabol et al. |
| 7,803,186 B1 | 9/2010 | Li |
| 8,167,935 B2 | 5/2012 | McGuckin, Jr. |
| 8,349,000 B2 | 1/2013 | Schreck |
| 8,475,512 B2 | 7/2013 | Hunt |
| 8,585,757 B2 | 11/2013 | Agathos |
| 8,637,144 B2 | 1/2014 | Ford |
| 8,709,077 B2 | 4/2014 | Schreck |
| 8,945,212 B2 | 2/2015 | Bruchman |
| 8,961,599 B2 | 2/2015 | Bruchman et al. |
| 9,504,565 B2 | 11/2016 | Armstrong |
| 2002/0045936 A1 | 4/2002 | Moe |
| 2002/0055773 A1 | 5/2002 | Campbell |
| 2002/0198594 A1 | 12/2002 | Schreck |
| 2003/0055496 A1 | 3/2003 | Cai |
| 2003/0097175 A1 | 5/2003 | O'Connor |
| 2003/0229394 A1 | 12/2003 | Ogle |
| 2004/0024448 A1 | 2/2004 | Chang et al. |
| 2004/0176839 A1 | 9/2004 | Huynh |
| 2004/0260393 A1 | 12/2004 | Rahdert |
| 2005/0261765 A1 | 11/2005 | Liddicoat |
| 2006/0154365 A1 | 7/2006 | Ratcliffe |
| 2006/0265053 A1 | 11/2006 | Hunt |
| 2007/0118210 A1 | 5/2007 | Pinchuk |
| 2009/0157175 A1 | 6/2009 | Benichou |
| 2010/0023114 A1 | 1/2010 | Chambers |
| 2010/0248324 A1 | 9/2010 | Xu et al. |
| 2011/0064781 A1 | 3/2011 | Cleek et al. |
| 2012/0078357 A1 | 3/2012 | Conklin |
| 2012/0116496 A1 | 5/2012 | Chuter |
| 2012/0123529 A1 | 5/2012 | Levi |
| 2012/0123530 A1 | 5/2012 | Carpentier |
| 2012/0253453 A1 | 10/2012 | Bruchman |
| 2012/0290082 A1 | 11/2012 | Quint |
| 2012/0323315 A1 | 12/2012 | Bruchman et al. |
| 2013/0166021 A1 | 6/2013 | Bruchman |
| 2014/0005773 A1 | 1/2014 | Wheatley |
| 2014/0163671 A1 | 6/2014 | Bruchman |
| 2014/0163673 A1 | 6/2014 | Bruchman |
| 2016/0001469 A1 | 1/2016 | Bacchereti |
| 2016/0074161 A1 | 3/2016 | Bennett |
| 2016/0113699 A1 | 4/2016 | Sverdlik |
| 2016/0317299 A1 | 11/2016 | Alkhatib |
| 2017/0042674 A1 | 2/2017 | Armstrong |

FOREIGN PATENT DOCUMENTS

| | | |
|---|---|---|
| JP | 2007536989 | 12/2007 |
| JP | 2010536527 | 12/2010 |
| WO | 000018333 A1 | 4/2000 |
| WO | 2000062716 A1 | 10/2000 |
| WO | WO-2002024118 A1 | 3/2002 |
| WO | WO-2002024119 A1 | 3/2002 |
| WO | 2002045933 A2 | 6/2002 |
| WO | 2002100301 A1 | 12/2002 |
| WO | WO-2003007795 A2 | 1/2003 |
| WO | WO-2003047468 A1 | 6/2003 |
| WO | WO-2005112827 A2 | 12/2005 |
| WO | WO-2009029199 A1 | 3/2009 |
| WO | WO-2009045332 A2 | 4/2009 |
| WO | WO-2010037141 A1 | 4/2010 |
| WO | WO-2012135603 A2 | 10/2012 |
| WO | WO-2013096854 A2 | 6/2013 |
| WO | WO-2015085138 A1 | 6/2015 |
| WO | WO-2016028591 A1 | 2/2016 |
| WO | WO-2016044223 A1 | 3/2016 |

OTHER PUBLICATIONS

International Preliminary Report on Patentability from PCT/US2015/045002, dated Mar. 2, 2017, 11 pages.

International Search Report and Written Opinion for PCT/US2014/068727 dated Mar. 2, 2015, corresponding to U.S. Appl. No. 14/561,148; 6 pages.

International Search Report and Written Opinion for PCT/US2015/050113, dated Nov. 24, 2015, 14 pages.

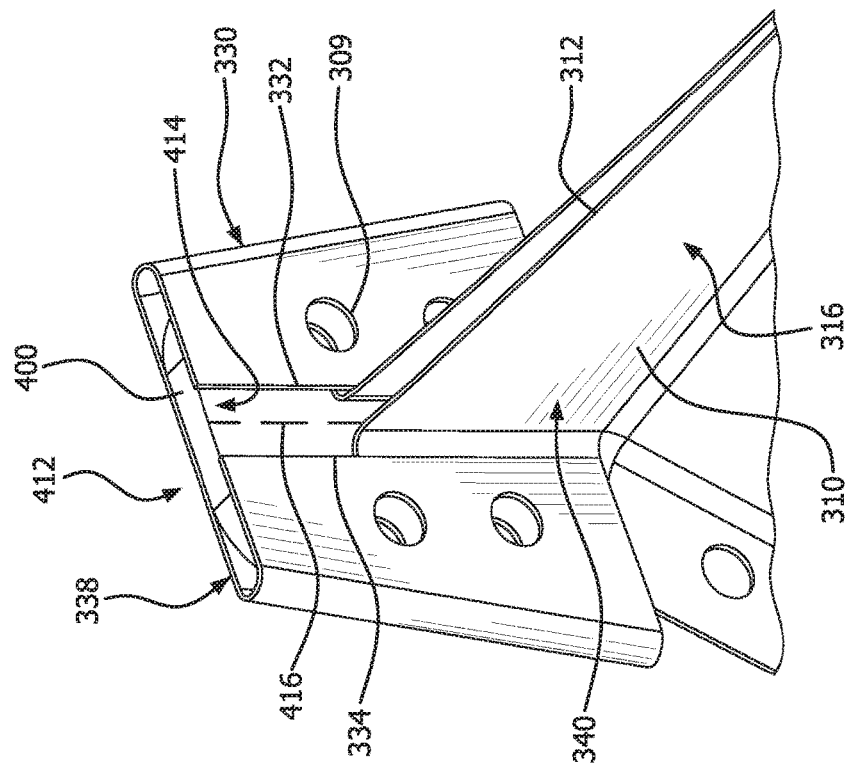
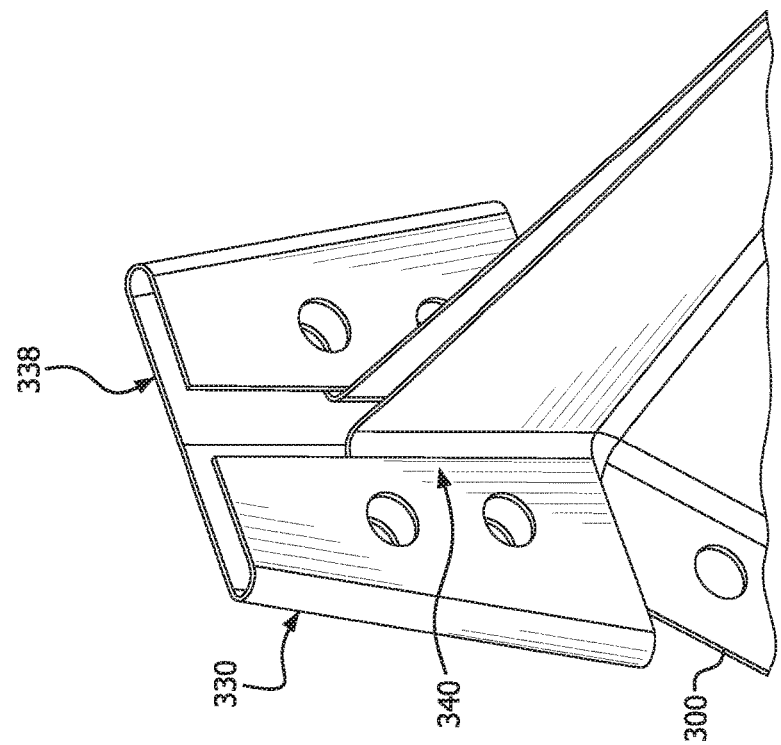

PROSTHETIC HEART VALVE WITH RETENTION ELEMENTS

CROSS-REFERENCE TO RELATED APPLICATION

This application is a continuation of U.S. patent application Ser. No. 14/853,654, filed Sep. 14, 2015, which claims the benefit of U.S. Provisional Application 62/050,628, filed Sep. 15, 2014, both of which are incorporated herein by reference in their entireties for all purposes.

FIELD

The present disclosure relates generally to prosthetic valves and more specifically flexible leaflet-type prosthetic heart valve devices.

BACKGROUND

A number of fabrication techniques have been used to couple the leaflets to a frame, including sewing individual leaflets to the frame (biological and synthetic), and for synthetic leaflets only, injection molding and dip coating a polymer onto the frame. In many cases, the resulting leaflet is supported on the frame and defines a flap having a mounting edge where the leaflet is coupled to the frame and a free edge that allows the flap to move. The flap moves under the influence of fluid pressure. In operation, the leaflets open when the upstream fluid pressure exceeds the downstream fluid pressure and closes when the downstream fluid pressure exceeds the upstream fluid pressure. The free edges of the leaflets coapt under the influence of downstream fluid pressure, closing the valve to prevent downstream blood from flowing retrograde through the valve.

Valve durability under the repetitive loads of the leaflets opening and closing is dependent, in part, on the load distribution between the leaflet and the frame. Further, substantial load is encountered on the leaflet when in the closed position. Mechanical failure of the leaflet can arise, for example, at the mounting edge, where the flexible leaflet is supported by the relatively rigid frame, particularly at the commissure posts. The repetitive loads of leaflet opening and closing leads to material failure by fatigue, creep or other mechanism, depending in part on the leaflet material. Mechanical failure at the mounting edge is especially prevalent with synthetic leaflets.

There remains a need for a more durable flexible leaflet prosthetic valve.

SUMMARY

Described embodiments are directed to apparatus, system, and methods for valve replacement, such as cardiac valve replacement. More specifically, described embodiments are directed toward flexible leaflet valve devices having biological or synthetic leaflet material and a frame, and methods of making and implanting the valve devices.

According to an embodiment, a prosthetic heart valve comprises a leaflet frame assembly. The leaflet frame assembly is an assembly of a leaflet frame, leaflet construct, and retention elements. The leaflet construct is that portion of the valve that comprises the leaflets and the structure for coupling the leaflets to the leaflet frame. In accordance with an embodiment, the leaflet construct defines a contiguous annular ring defining a plurality of leaflets and a bridge region between each of the leaflets. Each bridge region defines a bridge first end adjacent a first leaflet and a bridge second end adjacent a second leaflet. The leaflets extend radially inward from the leaflet frame when coupled to the leaflet frame. Each of the leaflets defines a fold-over portion that is folded over and lies against a leaflet frame outer side of the leaflet frame and coupled thereto such as with a securement structure, such as, but not limited to suture, adhesive, thermal bonding, or other means. Each of the bridge regions defines a bridge loop with a coaptation neck between the bridge loop and the adjacent leaflets. The coaptation neck is operable to pass through one of the post slots so that the bridge loop is adjacent to the outer portion of the leaflet frame and the leaflets extend radially inward from the leaflet frame. A retention element is disposed within the bridge loop effectively preventing the bridge loop from passing through the post slot. The retention element may be coupled to the commissure post, such as with a securement structure, such as, but not limited to suture, adhesive, thermal bonding, or other means. The fold-over portion of each of the leaflets is folded around an inflow edge of the leaflet frame and coupled thereto, such as with a securement structure, such as, but not limited to suture, adhesive, thermal bonding, or other means.

A method of making a prosthetic valve, in accordance with an embodiment, comprises obtaining a tube comprising one or more layers of expanded PTFE composite. Cutting a leaflet construct including a plurality of leaflets each being separated by a bridge region from the tube. Providing fold-over apertures in fold-over portions of the leaflets and bridge apertures in the bridge region. Obtaining a plurality of retention elements, each retention element defining retention element apertures. Folding each of the bridge regions into a bridge loop and defining a coaptation neck between each bridge loop and two adjacent leaflets, the bridge loops extending radially away from the tube axis. Disposing a retention element into each of the bridge loops. Suturing each retention element to the respective bridge loop passing suture through the bridge apertures and the retention element apertures that are aligned therewith. Cutting a leaflet frame from a metal tube defining leaflet frame windows and commissure posts therebetween where each commissure post defines a post slot dimensioned to receive a double thickness of the bridge region. Providing leaflet window frame apertures in the leaflet window frame and post apertures in the commissure posts. Disposing each coaptation neck in a respective post slot with the retention elements adjacent the post outer side and disposing the leaflets in the leaflet frame. Aligning the retention element apertures with the post apertures. Suturing each retention element to the respective commissure post passing suture through the retention element apertures and the post apertures that are aligned therewith. Folding the fold-over portions of each leaflet along the leaflet frame inflow edge and against the leaflet frame outer side aligning the fold-over apertures with the leaflet window frame apertures. And suturing each fold-over portion to the respective leaflet window frame passing suture through the fold-over apertures and the leaflet window frame apertures that are aligned therewith.

BRIEF DESCRIPTION OF THE DRAWINGS

The accompanying drawings are included to provide a further understanding of the present disclosure and are incorporated in and constitute a part of this specification, illustrate embodiments described herein, and together with the description serve to explain the principles discussed in this disclosure.

FIG. 5A is a perspective view of the bridge region formed into a bridge loop, in accordance with the embodiment of FIG. 2;

FIG. 5B is a perspective view of the bridge region formed into a bridge loop and containing a retention element, in accordance with the embodiment of FIG. 2;

DETAILED DESCRIPTION

Figure 1A:
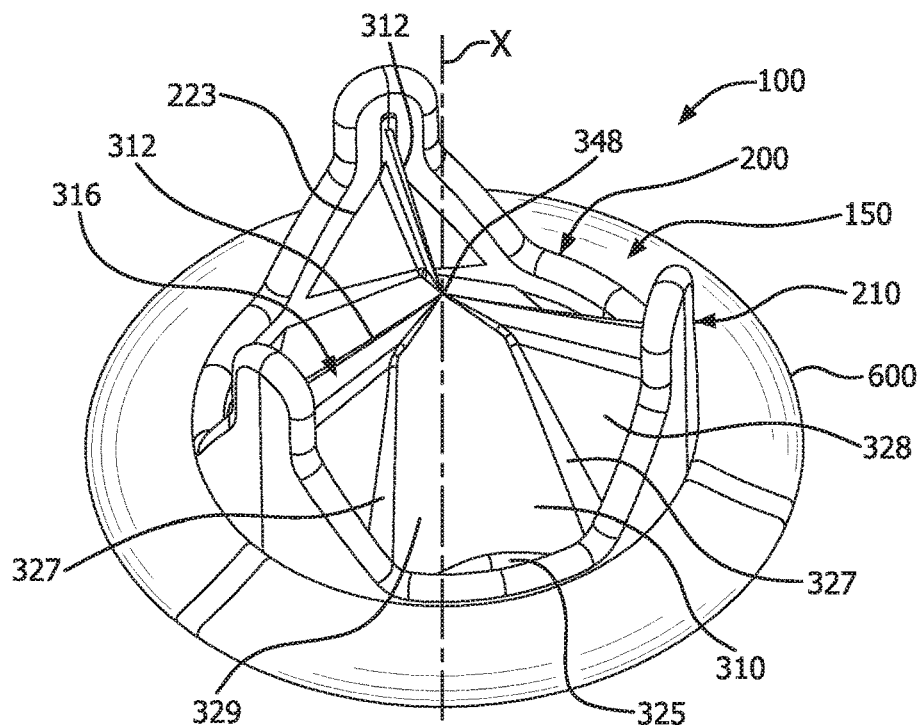
FIG. 1A is an outflow side perspective view of a prosthetic heart valve in accordance with an embodiment.

Persons skilled in the art will readily appreciate that various aspects of the present disclosure can be realized by any number of methods and apparatus configured to perform the intended functions. Stated differently, other methods and apparatus can be incorporated herein to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Although the embodiments herein may be described in connection with various principles and beliefs, the described embodiments should not be bound by theory. For example, embodiments are described herein in connection with prosthetic valves, more specifically cardiac prosthetic valves. However, embodiments within the scope of this disclosure can be applied toward any valve or mechanism of similar structure and/or function. Furthermore, embodiments within the scope of this disclosure can be applied in non-cardiac applications.

The term leaflet as used herein in the context of prosthetic valves is a flexible component of a one-way valve wherein the leaflet is operable to move between an open and closed position under the influence of a pressure differential. In an open position, the leaflet allows blood to flow through the valve. In a closed position, the leaflet substantially blocks retrograde flow through the valve. In embodiments comprising multiple leaflets, each leaflet cooperates with at least one neighboring leaflet to block the retrograde flow of blood. The pressure differential in the blood is caused, for example, by the contraction of a ventricle or atrium of the heart, such pressure differential typically resulting from a fluid pressure building up on one side of the leaflets when closed. As the pressure on an inflow side of the valve rises above the pressure on the outflow side of the valve, the leaflets open and blood flows therethrough. As blood flows through the valve into a neighboring chamber or blood vessel, the pressure on the inflow side equalizes with the pressure on the outflow side. As the pressure on the outflow side of the valve raises above the blood pressure on the inflow side of the valve, the leaflet returns to the closed position generally preventing retrograde flow of blood through the valve.

The term membrane as used herein refers to a sheet comprising a single material, such as, but not limited to, expanded fluoropolymer.

The term composite material as used herein refers to a combination of a membrane, such as, but not limited to, expanded fluoropolymer, and an elastomer, such as, but not limited to, a fluoroelastomer. The elastomer can be contained within a porous structure of the membrane, coated on one or both sides of the membrane, or a combination of coated on and contained within the membrane.

The term laminate as used herein refers to multiple layers of membrane, composite material, or other materials, such as elastomer, and combinations thereof.

The term film as used herein generically refers to one or more of the membrane, composite material, or laminate.

The term biocompatible material as used herein generically refers to any material with biocompatible characteristics including synthetic, such as, but not limited to, a biocompatible polymer, or a biological material, such as, but not limited to, bovine pericardium.

The terms native valve orifice and tissue orifice refer to an anatomical structure into which a prosthetic valve can be placed. Such anatomical structure includes, but is not limited to, a location wherein a cardiac valve may or may not have been surgically removed. It is understood that other anatomical structures that can receive a prosthetic valve include, but are not limited to, veins, arteries, ducts and shunts. It is further understood that a valve orifice or implant site may also refer to a location in a synthetic or biological conduit that may receive a valve.

As used herein, "couple" means to join, connect, attach, adhere, affix, or bond, whether directly or indirectly, and whether permanently or temporarily.

Embodiments herein include various apparatus, systems, and methods for a prosthetic valve, such as, but not limited to, cardiac valve replacement. The valve is operable as a one-way valve wherein the valve defines a valve orifice into which leaflets open to permit flow and close so as to occlude the valve orifice and prevent flow in response to differential fluid pressure.

Figure 1B:
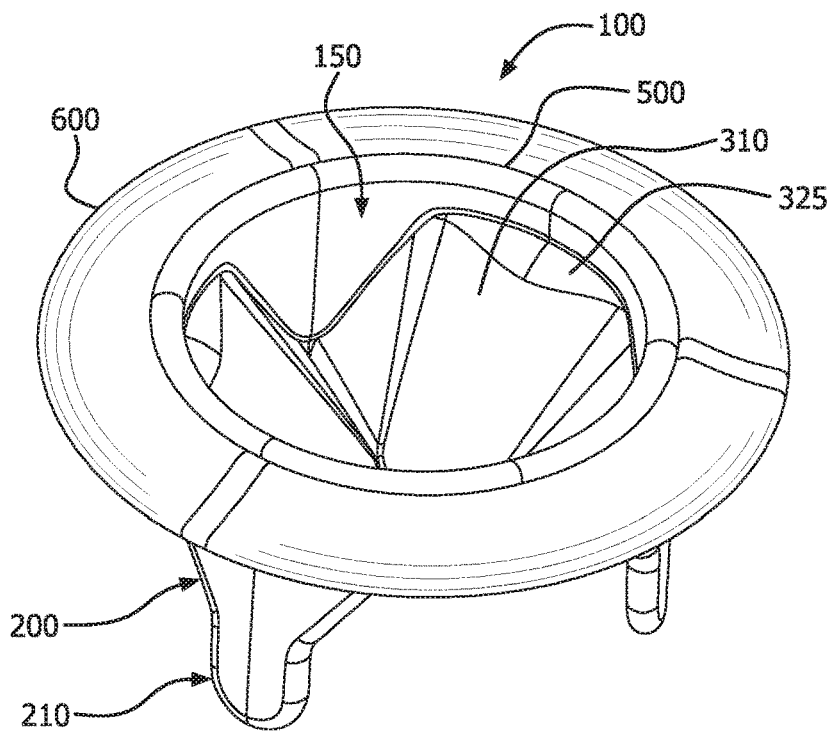
FIG. 1B is an inflow side perspective view of the embodiment of the valve of FIG. 1A.

FIGS. 1A and 1B are outflow and inflow, respectfully, perspective views of a valve 100 in the form of a prosthetic heart valve, in accordance with an embodiment. The components of the valve 100 that are visible in FIGS. 1A and 1B include three flexible leaflets 310, a leaflet frame 200 including three commissure posts 210 that has been covered with various material, a base frame 500 that has been covered with various material, and a sewing cuff 600. The leaflet free edges 312 of the leaflets 310 come together at a cooptation region 316 in a Y-shaped pattern (when viewed from above) to close the valve 100. The valve 100 closes in this fashion when the pressure of the blood on the outflow side (as viewed in FIG. 1A) is greater than the pressure of the blood on the inflow side of the valve (as viewed in FIG. 1B). The leaflet free edges 312 of the leaflets 310 move apart to open the valve 100 and to let blood flow through the valve 100 from the inflow side as viewed in FIG. 1B when the pressure of the blood on the inflow side of the valve 100 is greater than the pressure on the outflow side of the valve 100.

FIGS. 2-5B show various components that are included in the valve 100, in accordance with an embodiment.

Figure 2:
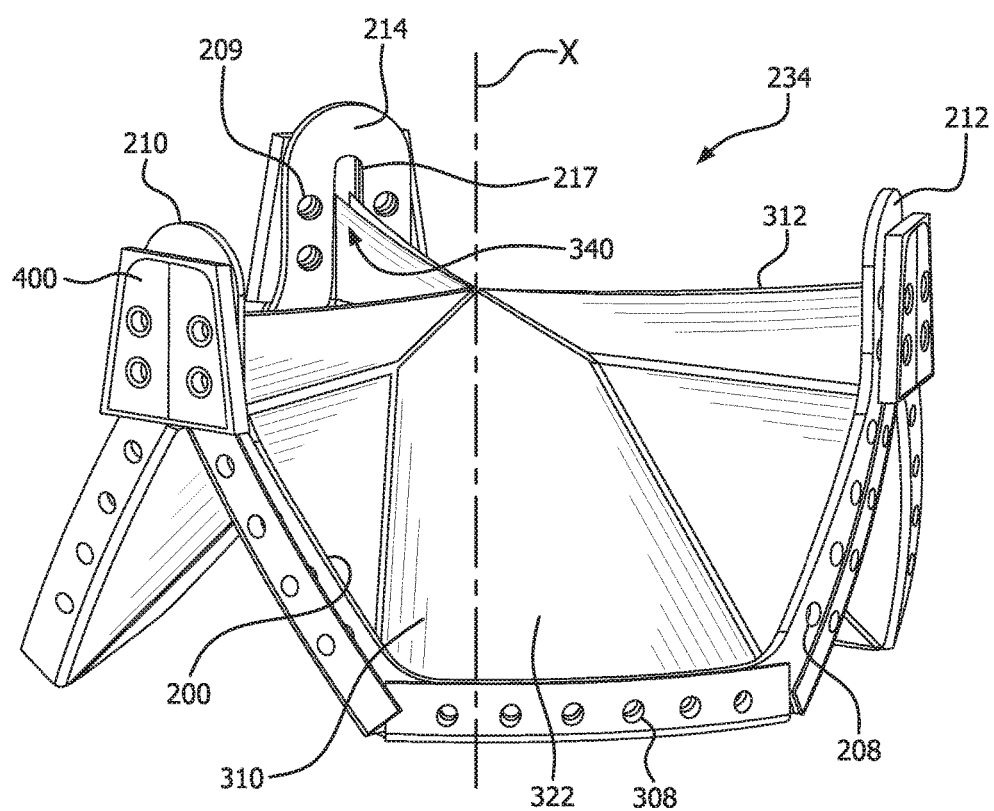
FIG. 2 is a perspective view of a leaflet frame assembly of the embodiment of the valve of FIG. 1A.
Figure 3:
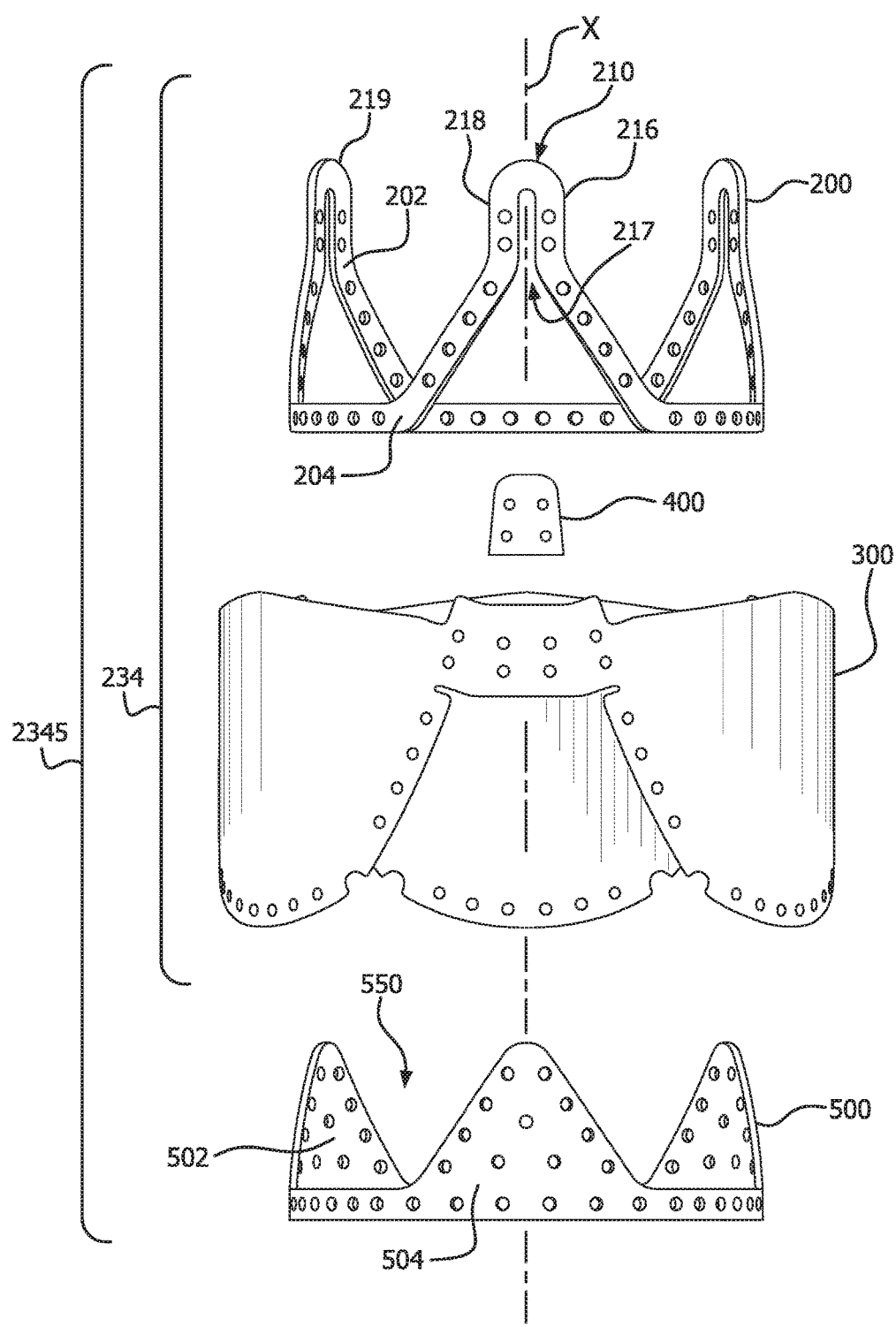
FIG. 3 is a side exploded view of the leaflet frame, retention element, leaflet construct and base frame, of an embodiment of a valve.
Figure 4:
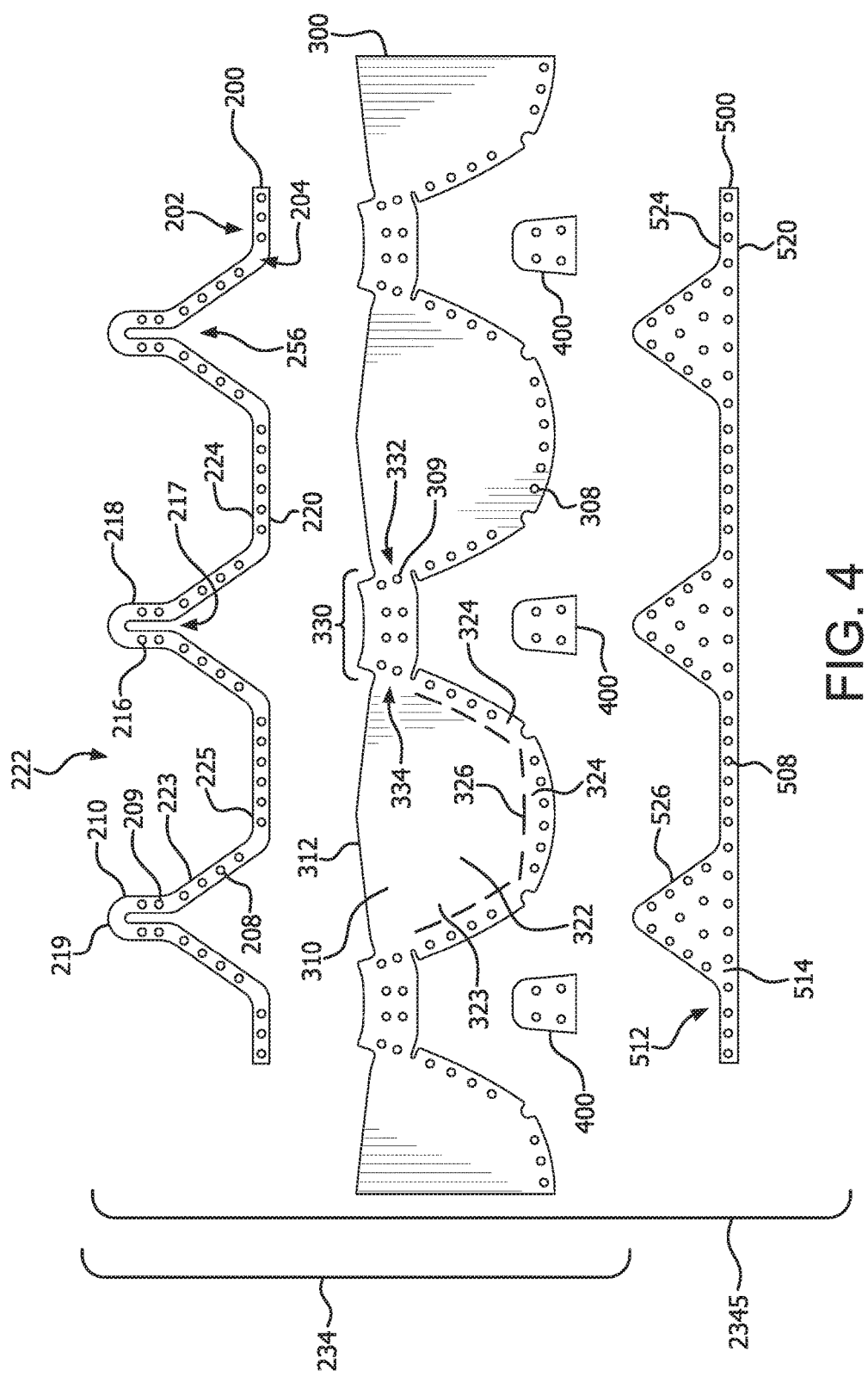
FIG. 4 is a representation of the embodiment of the valve of FIG. 3 unrolled to a flat orientation, in accordance with an embodiment.

FIG. 2 is a perspective view of a leaflet frame assembly 234, in accordance with an embodiment, also shown in FIG. 3 in an exploded view and shown in FIG. 4 in an exploded view wherein the annular components have been longitudinally cut and laid open, so as to better illustrate the elements of the valve components. The leaflet frame assembly 234 comprises a leaflet frame 200, a leaflet construct 300, and a plurality of retention elements 400.

Leaflet Frame

The leaflet frame 200 is operable to hold and support the leaflet construct 300. The leaflet frame 200 is annular, that is it defines a cylinder having an axis X and a plurality of commissure posts 210 extending parallel to the axis x that are spaced from one another, each commissure post 210 defining a post slot 217 therethrough that is aligned parallel to the axis X. Between the commissure posts 210 is a leaflet window 222 that is operable to couple to and support the leaflet 310 around the perimeter of the leaflet 310 except for the leaflet free edge 312.

The leaflet frame 200 defines a cylinder having a leaflet frame inner side 202 and a leaflet frame outer side 204 opposite the leaflet frame inner side 202. The leaflet frame 200 further defines a plurality of commissure posts 210. Each commissure post 210 has a post outer side 212 and a post inner side 214 opposite the post outer side 212. The commissure post 210 is defined by a first post leg 216 and a second post leg 218 separated by a post slot 217 therebetween. A commissure tip 219 couples the first post leg 216 and the second post leg 218.

In accordance with an embodiment, the leaflet frame 200 is annular about a central longitudinal axis X of the valve 100 as shown in FIGS. 2 and 3. The leaflet frame 200 defines a plurality of leaflet windows 222 that follow the shape of the leaflet 310. In accordance with an embodiment, each of the leaflet windows 222 includes two leaflet window sides 223 and a leaflet window base 225, defining three sides of an isosceles trapezoid, wherein the leaflet window base 225 is substantially flat. The leaflet base 325 is coupled to the leaflet window base 225 and each of the two leaflet sides 323 are coupled to one of the two leaflet window sides 223. The adjacent leaflet window sides 223 are interconnected by a commissure post 210 comprising of a first post leg 216 and a second post leg 218 that extend from adjacent leaflet window sides 223 and meet at a commissure tip 219. The commissure posts 210 are equally spaced from one another around the leaflet frame 200. The first post leg 216 and the second post leg 218 define a post slot 217 therebetween.

The leaflet frame 200 can be etched, cut, laser cut, stamped, three-dimensional printed, among other suitable processes, into an annular structure or a sheet of material, with the sheet then formed into an annular structure.

The leaflet frame 200 can comprise, such as, but not limited to, any elastically deformable metallic or polymeric material that is generally biocompatible. The leaflet frame 200 can comprise a shape-memory material, such as nitinol, a nickel-titanium alloy. Other materials suitable for the leaflet frame 200 include, but not limited to, other titanium alloys, stainless steel, cobalt-nickel alloy, polypropylene, acetyl homopolymer, acetyl copolymer, other alloys or polymers, or any other material that is generally biocompatible having adequate physical and mechanical properties to function as a leaflet frame 200 as described herein.

Leaflet Construct

The leaflet construct 300 is that portion of the valve 100 that comprises the leaflets 310 and the structure for coupling the leaflets 310 to the leaflet frame 200. In accordance with an embodiment, the leaflet construct 300 defines a contiguous annular ring defining a plurality of leaflets 310 and a bridge region 330 between each of the leaflets 310. As used herein, contiguous means without a break or a seam, that is, seamless. Each bridge region defines a bridge first end 332 adjacent a first leaflet 310 and a bridge second end 334 adjacent a second leaflet 310. The leaflets extend radially inward from the leaflet frame 200 when coupled to the leaflet frame 200. Each of the leaflets 310 define a fold-over portion 324 that is folded over and lies against a leaflet frame outer side 204 of the leaflet frame 200 and coupled thereto. Each of the bridge regions 330 defines a bridge loop 338 with a coaptation neck 340 between the bridge loop 338 and the adjacent leaflets 310. The coaptation neck 340 is operable to pass through one of the post slots 217 so that the bridge loop 338 is adjacent to the outer portion of the leaflet frame 200 and the leaflets 310 extend radially inward from the leaflet frame 200.

The leaflet construct 300 comprising the flexible leaflets 310 can be made of polymer. For example, pre-shaped polymer leaflets can be made by starting from a cylinder of polymer material that has been cut into a shape like that shown in FIGS. 3 and 4.

The leaflet construct 300 can also be made from a sheet of polymer material that has been cut into a shape like that shown in FIGS. 3 and 4 and subsequently coupled together into an annular shape. A leaflet construct 300 having a seam, though may not have the advantages of a contiguous, seamless construct that may exhibit a higher tensile strength characteristics. The advantages provided by the retention element 400 may still be realized.

Another way that the leaflet construct 300 may be formed (assuming the use of a material for the leaflets that is suitable for formation in this way) is by compression or injection molding.

In accordance with an embodiment, each leaflet 310, at the folds 326, has substantially the shape of an isosceles trapezoid having two leaflet sides 323, a leaflet base 325 and a leaflet free edge 312 opposite the leaflet base 325, corresponding to the two leaflet window sides 223 and a leaflet window base 225. The two leaflet sides 323 diverge from the leaflet base 325, wherein the leaflet base 325 is substantially flat.

In accordance with other embodiments of the valve 100, each leaflet 310 includes a central region 329 and two side regions 328 on opposite sides of the central region 329. The central region 329 is defined by a shape substantially that of an isosceles trapezoid defined by two central region sides 327, the leaflet base 325 and the leaflet free edge 312. Each of the side regions 328 has a shape substantially that of a triangle and each are defined by one of the central region sides 327, one of the leaflet sides 323, and the leaflet free edge 312.

In accordance with another embodiment, the leaflet window may be described as having a U-shape. The leaflet frame generally defines a plurality of U-shaped portions as one proceeds annularly around the leaflet frame, defining a plurality of commissure posts and a plurality of leaflet window frame portions.

As shown in FIG. 4, each of the leaflets 310 has a leaflet belly portion 322, and a fold-over portion 324. The leaflet belly portion 322 of each leaflet 310 is the operating portion of the leaflet 310 when in a finished and implanted valve 100. The fold-over portion 324 of each leaflet 310 is the portion that is used to secure the leaflet 310 to the two leaflet window sides 223 and the leaflet window base 225 of the leaflet frame 200. Each leaflet window side 223 and a leaflet window base 225 of the leaflet frame 200 fits into a fold 326 that is formed between the leaflet belly portion 322 and the fold-over portion 324 of a respective one of the leaflet sides 323 and leaflet base 325, respectively, of the leaflets 310, as shown in FIG. 2. The leaflet belly portion 322 of each leaflet 310 includes enough material between the commissure posts 210 of the leaflet frame 200 so that the leaflet free edge 312 of the three leaflet belly portions 322 can come together or coapt in the interior of the valve 100 to close the valve 100 as shown in FIG. 1.

Figure 6:
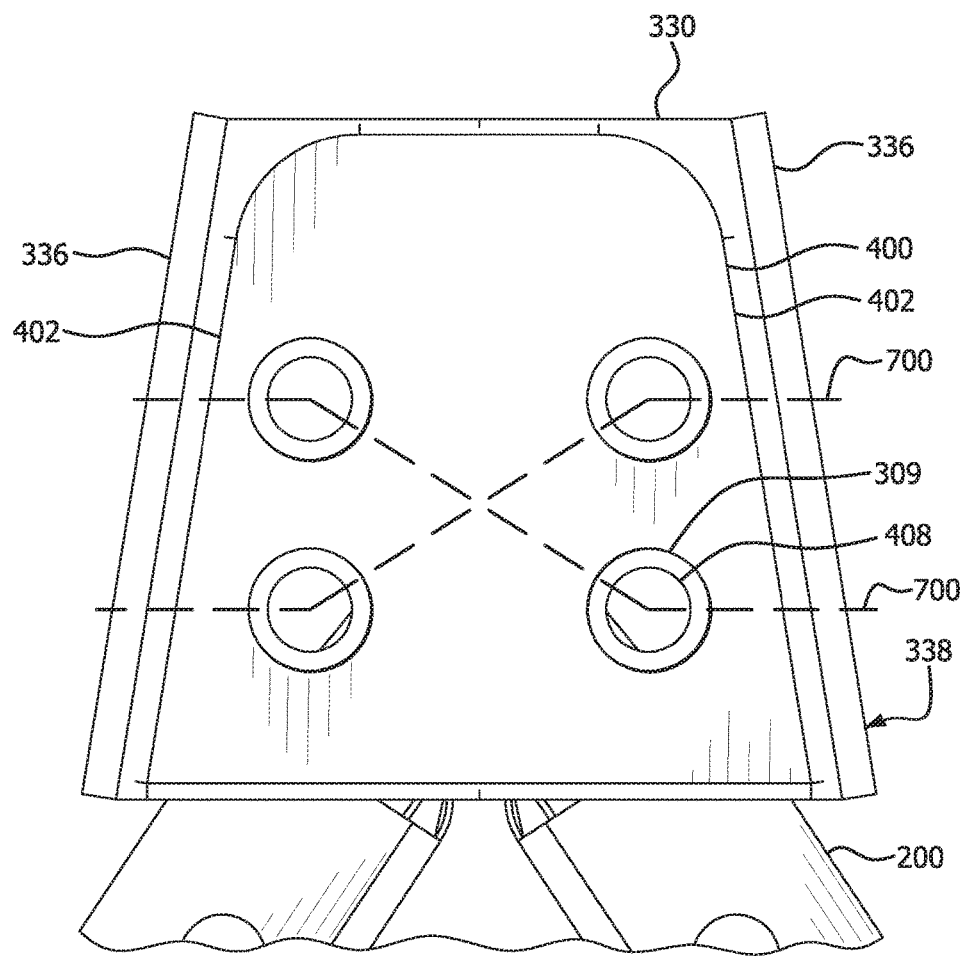
FIG. 6 is a side view of the bridge region of the embodiment of FIG. 7.

Between each of the leaflets 310 is a bridge region 330, as shown in FIGS. 4, 5A, 5B and 8. The bridge region 330 is operable to be formed into a bridge loop 338 having a generally rectangular shape, folding about two loop fold lines 336 so as to contain the retention element 400 therein as discussed below, as shown in FIGS. 5A, 5B, 6 and 8. Due to the curvature of the annular leaflet frame 200, the two loop fold lines 336 form an angle alpha, which corresponds to the retention element sides 402 as shown in FIG. 6, in accordance with an embodiment.

In accordance with an embodiment, the leaflet construct 300 can comprise a biocompatible material that is not of a biological source and that is sufficiently compliant and strong for the particular purpose, such as a biocompatible polymer. In an embodiment, the leaflet construct 300 comprises a membrane that is combined with an elastomer to form a composite material. In accordance with other embodiments, the biocompatible material that makes up the leaflet construct 300 comprises a biological material, such as, but not limited to, bovine pericardium.

The shape of the leaflets 310 are defined in part by the shape of the leaflet frame 200 and the leaflet free edge 312. The shape of the leaflets 310 can also be defined by the structures and processes used to manufacture the valve 100, such as, but not limited, those described below. For example, in accordance with an embodiment, the shape of the leaflets 310 also depends in part on molding the leaflets 310 using molding and trimming processes to impart a predetermined shape to the leaflet 310.

The leaflets 310 generally flex about the leaflet base 325 about the leaflet window base 225 of the U-shaped portion as the leaflets 310 open and close. In an embodiment, when the valve 100 is closed, generally about half of each leaflet free edge 312 abuts an adjacent half of a leaflet free edge 312 of an adjacent leaflet 310, as shown in FIG. 1A. The three leaflets 310 of the embodiment of FIG. 1A meet at a triple point 348. The valve orifice 150 is occluded when the leaflets 310 are in the closed position stopping fluid flow.

Leaflet Construct Material

The leaflet construct 300 can comprise any biocompatible material sufficiently compliant and flexible, such as a biocompatible polymer. The leaflet construct 300 can comprise a membrane that is combined with an elastomer to form a composite material. The leaflet construct 300 can comprise, according to an embodiment, a composite material comprising an expanded fluoropolymer membrane, which comprises a plurality of spaces within a matrix of fibrils, and an elastomeric material. It should be appreciated that multiple types of fluoropolymer membranes and multiple types of elastomeric materials can be combined to form a composite material while remaining within the scope of the present disclosure. It should also be appreciated that the elastomeric material can include multiple elastomers, multiple types of non-elastomeric components, such as inorganic fillers, therapeutic agents, radiopaque markers, and the like while remaining within the scope of the present disclosure.

In accordance with an embodiment, the composite material includes an expanded fluoropolymer material made from porous ePTFE membrane, for instance as generally described in U.S. Pat. No. 7,306,729 to Bacino.

The expandable fluoropolymer, used to form the expanded fluoropolymer material described, can comprise PTFE homopolymer. In alternative embodiments, blends of PTFE, expandable modified PTFE and/or expanded copolymers of PTFE can be used. Non-limiting examples of suitable fluoropolymer materials are described in, for example, U.S. Pat. No. 5,708,044, to Branca, U.S. Pat. No. 6,541,589, to Baillie, U.S. Pat. No. 7,531,611, to Sabol et al., U.S. patent application Ser. No. 11/906,877, to Ford, and U.S. patent application Ser. No. 12/410,050, to Xu et al.

The expanded fluoropolymer membrane can comprise any suitable microstructure, such as pores, for achieving the desired leaflet performance. Other biocompatible polymers which can be suitable for use in leaflet include but are not limited to the groups of urethanes, silicones (organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing.

Further examples of leaflet construct materials include: wherein the leaflet construct comprises at least one fluoropolymer membrane layer; wherein the leaflet construct comprises a laminate having more than one fluoropolymer membrane layer; wherein the at least one fluoropolymer membrane layer is an expanded fluoropolymer membrane layer; wherein an elastomer is contained within the expanded fluoropolymer membrane layer; wherein the elastomer comprises perfluoromethyl vinyl ether and tetrafluoroethylene; wherein the expanded fluoropolymer membrane layer comprises ePTFE; wherein the leaflet construct comprises a composite material having at least one fluoropolymer membrane layer having a plurality of pores and an elastomer present in the pores of at least one of the fluoropolymer membrane layers; wherein the composite material comprises fluoropolymer membrane by weight in a range of about 10% to 90%; wherein the elastomer comprises (per)fluoroalkylvinylethers (PAVE); wherein the elastomer comprises a copolymer of tetrafluoroethylene and perfluoromethyl vinyl ether; wherein the elastomer is silicone; wherein the elastomer is a fluoroelastomer; wherein the elastomer is a urethane; and wherein the elastomer is a TFE/PMVE copolymer; wherein the TFE/PMVE copolymer comprises essentially of between about 40 and 80 weight percent perfluoromethyl vinyl ether and complementally 60 and 20 weight percent tetrafluoroethylene; and wherein the leaflet construct comprises silicone.

Retention Element

The retention element 400 is an element that is operable to be disposed within the bridge loop 338 formed by the bridge region 330 of the leaflet construct 300, which effectively prevents the bridge loop 338 from passing through the post slot 217, and therefore the leaflet construct 300 is mechanically coupled to the commissure post at the post outer side. The retention element 400 has a width that is larger than a width of the post slot 217. With the retention element 400 being disposed in the bridge loop 338, the bridge loop 338 will be prevented from passing through the post slot 217. The size of the bridge loop 338 should correspond closely to the size of the retention element 400 to prevent a portion of the bridge region 330 from extending through the post slot 217 to the valve orifice 150 in case of the suture loosening or failing.

Figure 8:
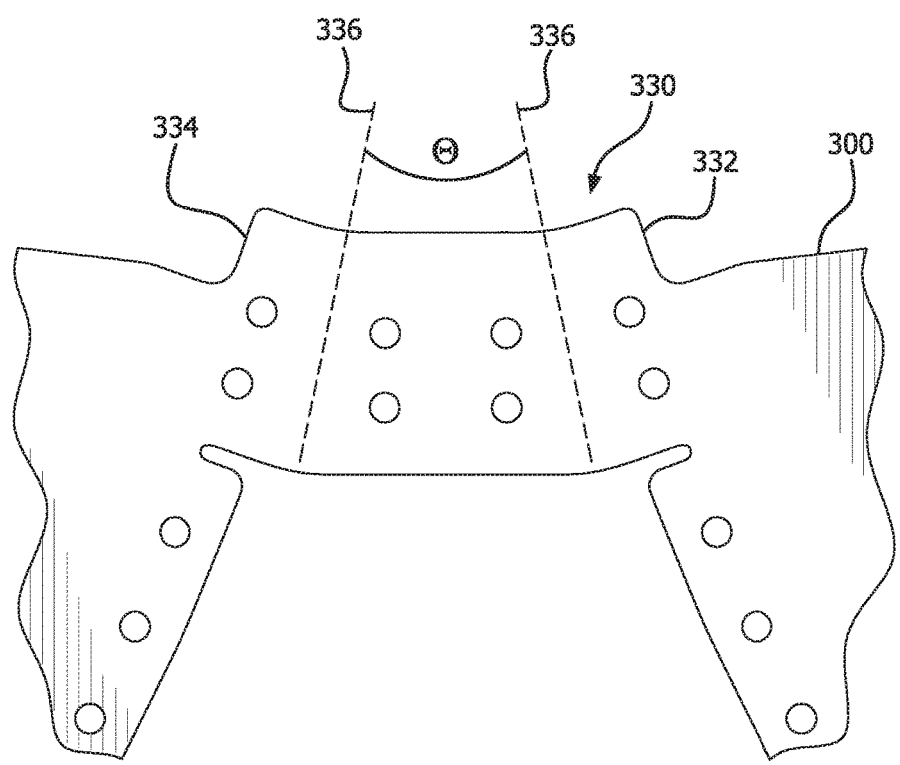
FIG. 8 is a side view of the bridge region showing fold line at an angle alpha, in accordance with another embodiment.

In accordance with an embodiment, the retention element 400 defines a relatively flat generally rectangular shape so as to have a low profile on the post outer side 212 of the commissure post 210. Due to the curvature of the annular leaflet frame 200, the sides of the retention element 400 are formed at an angle corresponding to the two loop fold lines 336 that form an angle alpha, as shown in FIG. 8, in accordance with an embodiment.

In accordance with embodiments, the retention element 400 can be flat, relatively flat, or concave on the inside (toward the center of the valve) to correspond with the radially outer convexity of commissure post 210 that the retention element 400 will be adjacent to. Each retention element 400 has a plurality of retention element apertures 408 that align with commissure post apertures 209 wherein the retention element 400 is placed against the post outer side 212 of the commissure post 210 with a portion of the bridge region 330 therebetween. A securement structure, such as, but not limited to suture 700, may be used to couple the retention element 400 to the commissure post 210. Suture may be of any suitable material, such as PTFE, PET, and nylon, among others. Stitching comprising suture 700 may be passed through these aligned commissure post apertures 209 and retention element apertures 408 and the bridge region 330 to hold each retention element 400 and the bridge region 330 to the commissure post 210. Some or all of this suture 700 may pass through the fold-over portion 324 of the leaflet 310. In that event, this suture 700 will contribute to securing the leaflet belly portion 322 of the leaflets 310 to the leaflet frame 200.

Examples of suitable materials for the retention elements 400 include various biocompatible alloys such as titanium, Elgiloy, MP35N, stainless steel, nitinol, etc., and various biocompatible engineering plastics such as acetyl polymers, PTFE, and PEEK.

Leaflet Frame Assembly

A leaflet frame assembly 234 is the assembly of the leaflet frame 200, leaflet construct 300, and the retention elements 400. The leaflet construct 300 is that portion of the valve 100 that comprises the leaflets 310 and the structure for coupling the leaflets 310 to the leaflet frame 200. In accordance with an embodiment, the leaflet construct 300 defines a contiguous cylinder defining a plurality of leaflets 310 and a bridge region 330 between each of the leaflets 310. Each bridge region defines a bridge first end 332 adjacent a first leaflet 310 and a bridge second end 334 adjacent a second leaflet 310. The leaflets extend radially inward from the leaflet frame 200 when coupled to the leaflet frame 200. Each of the leaflets 310 defines a fold-over portion 324 that is folded over and lies against a leaflet frame outer side 204 of the leaflet frame 200 and coupled thereto, such as with securement structure, such as, but not limited to suture, adhesive, thermal bonding, or other means. Each of the bridge regions 330 defines a bridge loop 338 with a coaptation neck 340 between the bridge loop 338 and the adjacent leaflets 310. The coaptation neck 340 is operable to pass through one of the post slots 217 so that the bridge loop 338 is adjacent to the outer portion of the leaflet frame 200 and the leaflets 310 extend radially inward from the leaflet frame 200. A retention element 400 is disposed within the bridge loop 338 effectively preventing the bridge loop 338 from passing through the post slot 217. The retention element 400 may be coupled to the commissure post 210, such as with suture, adhesive, thermal bonding, or other means. The fold-over portion 324 of each of the leaflets 310 is folded around an inflow edge of the leaflet frame 200 and coupled thereto, such as with suture, adhesive, thermal bonding, or other means.

In accordance with an embodiment, each bridge region 330 is wrapped around a retention element outer side 412 to the retention element inner side 414 of one of the retention elements 400 with the bridge first end 332 wrapped across the retention element inner side 414 to adjacent a dividing line 416 that vertically bisects the retention element 400, from a first direction and the bridge second end 334 wrapped across the retention element inner side 414 to adjacent the dividing line 416 from an opposite direction, wherein the bridge first end 332 and bridge second end 334 are adjacent to each other to define a coaptation neck 340.

In accordance with an embodiment, the leaflet frame assembly 234 is provided with means for coupling to a native tissue annulus, and thus the leaflet frame assembly 234 is a prosthetic heart valve 100. In an embodiment, a sewing cuff 600 is coupled to the leaflet frame assembly 234, where the sewing cuff is operable to be sutured to the native tissue annulus. In another embodiment, a base frame 500 comprising a sewing cuff 600 is coupled to the leaflet frame assembly 234.

One possible way to characterize the benefits of some embodiments presented herein is the effect of the bridge region 330 being a continuous member, that is, no seams or breaks. Any force tending to pull or extract the bridge region 330 through the post slot 217 is countered by the tensile strength of the material that the bridge region 330 comprises. The forces on the leaflets 310 during use are greatest at the commissure posts 210 tending to pull the leaflets 310 away from the commissure posts 210. The coupling of the leaflet construct 300 to the leaflet frame 200 at the commissure posts 210, in accordance with these embodiments, does not rely solely on the suture 700 but also the retention element 400 that prevents the bridge region 330 from passing through the post slot 217. It is understood that sutures, in general, tend to loosen and fail over a period of time, especially in regions of high stress. In these embodiments, the suture 700 that couples the bridge region 330 to the commissure post 210 may loosen or fail but the retention element 400 continues to prevent the bridge region 330 from passing through the post slot 217 preventing failure of the valve 100.

Further, the retention element 400 provides a clamping force between a portion of the bridge region 330 and the post outer side 212 of the commissure post 210 during operation of the valve 100. This clamping force is the result of the retention element 400 being larger than the post slot 217 which prevents the bridge region 330 from passing through the post slot 217. The clamping force does not rely on the strength of the suture 700 or the tension of the suture on the bridge region 330 and the commissure posts 210.

This clamping force may tend to distribute the forces on the bridging region 330 reducing peak stresses that might be applied at the suture 700 and apertures 999. Further the clamping force is the primary mode of transferring the forces from the leaflets 130 to the leaflet frame 200 rather than merely relying on the stitching of the leaflets 310 to the leaflet frame 200. Further, the angle alpha of the two loop fold lines 336 allows for a substantially equal distribution of stresses over the coaptation neck 340 between the bridge loop 338 and the adjacent leaflets 310 whereby reducing the peak stresses in the coaptation neck 340.

In accordance with these embodiments, the leaflets 310 extend perpendicular from the leaflet frame 200, as shown in FIG. 5. The leaflets 310 extend from the post slot 217 in a direction perpendicular to the post inner side 214 As such, the leaflets 310 exhibit a bias toward the closed position. This is beneficial in that the valve 100 will tend to close earlier during the phase of the cardiac cycle where the blood is decelerating or reversing. An earlier closure will tend to reduce back flow through the valve 100.

The design and manufacturing process (including the various components and the way of assembling those components) greatly reduce possible stress concentration at the leaflet frame-leaflet junction by distributing the load more evenly. These design and manufacturing process aspects also (1) reduce the burden of extensive and demanding suturing, (2) increase the consistency of valve manufacturing results, and (3) increase the service life of a resulting valve as a consequence of all of the foregoing factors.

Instead of or in addition to suture, chemical bonds and/or adhesives can be used between the leaflet frame 200 and the fold-over portion 324 of the leaflet construct.

The bridge regions 330 are passed through the post slot 217 in a number of ways. In accordance with an embodiment, the bridge region 330 is formed into a narrow bridge loop 338 which is passed through the post slot 217 from the leaflet frame inner side 202 to the leaflet frame outer side 204. A retention element 400 may then be inserted into the bridge loop 338 preventing the bridge loop 338 from being passed back through the post slot 217.

Figure 7:
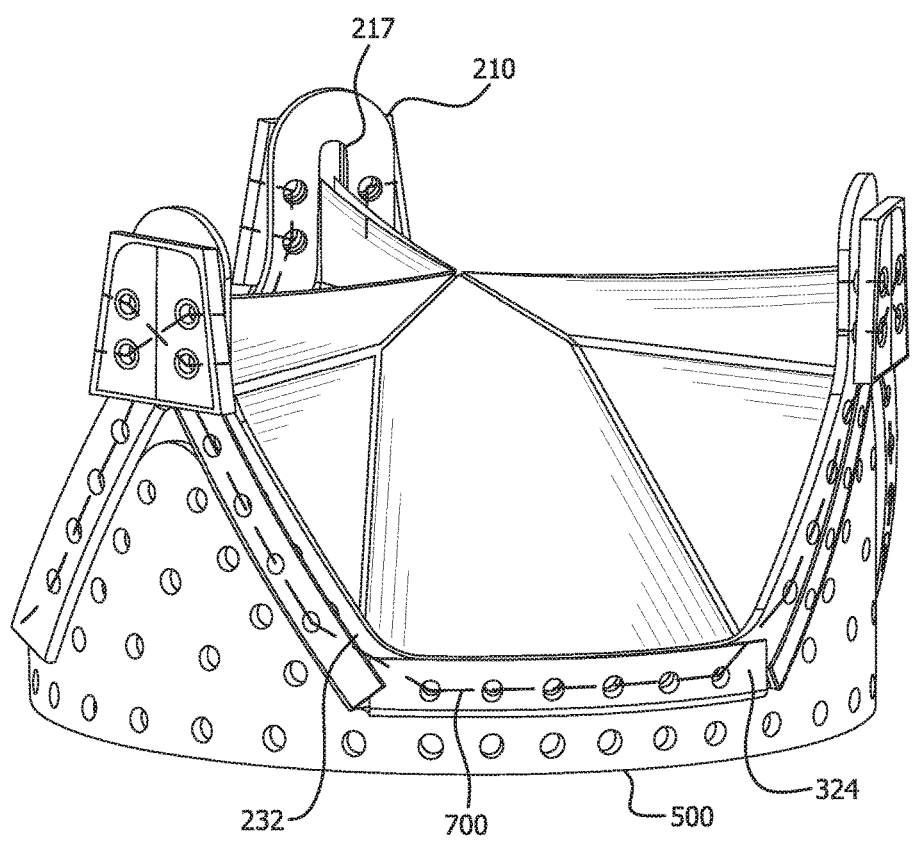
FIG. 7 is a perspective view of a leaflet frame assembly and a base frame, in accordance with the embodiment of the valve of FIG. 1A.

In accordance with embodiments, the leaflet frame 200, leaflet construct 300 and the retention elements 400 have matching and radially aligned apertures for receiving suture. The fold-over portion 324 and the bridge regions 330 containing a retention element 400 are coupled to the leaflet frame by suturing through these matching apertures. The dashed lines in FIG. 7 show an illustrative suture pattern. The suturing work-load is very light and not skill-demanding.

Base Frame

The base frame 500 is a generally annular member defining a base frame lumen 550 having a base frame inner side 502 and a base frame outer side 504, as shown in FIGS. 3 and 4. The base frame 500 may provide structural, load-bearing support to the leaflet frame 200. In addition, the base frame 500 can be configured to provide positive engagement to the recipient tissue at the implantation site.

In accordance with an embodiment, the base frame 500 defines a plurality of triangular regions 526 extending away from the base frame inflow edge 520. The leaflet frame 200 may comprise corresponding triangular openings 256 defined by two leaflet window sides 223 of adjacent leaflet windows 222 of the leaflet frame 200 define two sides of an isosceles triangle on the leaflet frame inflow edge 220. The triangular openings 256 are operable to receive the triangular regions 526 of the base frame 500 therein.

The base frame 500 can comprise any metallic or polymeric material that is generally biocompatible. For example, the base frame 500 can comprise a material, such as, but not limited to nitinol, cobalt-nickel alloy, stainless steel, and polypropylene, acetyl homopolymer, acetyl copolymer, ePTFE, other alloys or polymers, or any other biocompatible material having adequate physical and mechanical properties to function as described herein.

The base frame 500 can be etched, cut, laser cut, or stamped into a tube or a sheet of material, with the sheet then formed into an annular structure.

In accordance with embodiments, the base frame 500 can be configured to provide positive engagement to an implant site. In another embodiment, the valve 100 further includes a sewing cuff 600 coupled about the base frame 500, as shown in FIGS. 1A and 1B, that is operable to accept suture so as to be sewn to a tissue orifice. It is understood that conventional, surgical techniques to implant prosthetic valves can be used to implant the valve 100, in accordance with embodiments.

It is appreciated that other elements or means for coupling the valve 100 to an implant site are anticipated. By way of example, but not limited thereto, other means, such as mechanical and adhesive means may be used to couple the valve 100 to a synthetic or biological conduit.

In another embodiment, the valve 100 further comprises a base frame 500, as shown in FIGS. 3 and 4. The base frame 500 is coupled to a leaflet frame inflow edge 220 of the leaflet frame 200. The base frame 500 is provided with base frame apertures 508 that may be used to suture the base frame 500 to the leaflet frame 200 using suture 700. An advantage of a separate leaflet frame 200 and base frame 500 is that they may have different physical characteristics. By way of example, a relatively less stiff leaflet frame 200 supporting the leaflets 310 can be more likely to reduce the loading encountered by the opening and closing leaflets 130 as compared to a stiffer leaflet frame 200. The leaflet frame 200 having a relatively less stiff property may reduce leaflet accelerations and reduce the closing stresses on the leaflets 310. Wherein the base frame 500 may be more stiff which would be more suitable for suturing to the native tissue orifice. The base frame 500 may resist the compressive forces that may be encountered at the implant site, for example.

In embodiments of the valve 100, the inclusion of a base frame 500 and a leaflet frame 200 provides a means for providing different physical properties for each of the base frame 500 and the leaflet frame 200 suitable for a particular purpose. In accordance with an embodiment, the base frame 500 is stiffer as compared with the leaflet frame 200. The base frame 500, when engaged to the implant site, such as, but not limited to a tissue orifice, is rigid enough to not significantly deform under physiological loading.

The physical properties of the base frame 500 and the leaflet frame 200 depends, in part, on the size, shape, thickness, and material property of the base frame 500 and the leaflet frame 200.

Stiff and stiffness, as used herein and as is commonly used in engineering, is a measure of the resistance to deformation given by a base. Stiff and stiffness is a function of, among other things, material properties, the shape of the object, and the boundary conditions on the object. Stiffness of the leaflet frame 200 (see FIG. 1A) may be measured by any number of methods known in the art. In accordance with one method, cables may be coupled to each of the three commissure posts 210 and brought together so as to allow the cables to be pulled simultaneously along the axis of the leaflet frame, with the leaflet frame held by the base frame 500. The amount of force on the cables required to deflect the three commissure posts toward the axis provides a measure of stiffness. The same may be done with the base frame 500 with the cables coupled to three equally spaced points on the base frame, such as an apex of the triangular region 526, as shown in FIG. 4.

Sewing Cuff

The valve 100 may be provided with a sewing cuff 600 adjacent the base frame 500, as shown in FIGS. 1A and 1B. The sewing cuff 600 is operable to provide structure that receives suture for coupling to the implant site. The sewing cuff 600 may comprise any suitable material, such as, but not limited to, double velour polyester and silicone. The sewing cuff 600 may be located circumferentially around the base frame 500 or perivalvular depending from the base frame

500. The sewing cuff 600 may comprise a filler material, such as, but not limited to, a silicone ring and/or PTFE felt.

Methods

A method of making a prosthetic valve, in accordance with embodiment, comprises obtaining a tube comprising one or more layers of expanded PTFE composite. Cutting a leaflet construct including a plurality of leaflets each being separated by a bridge region from the tube. Providing fold-over apertures in fold-over portions of the leaflets and bridge apertures in the bridge region. Obtaining a plurality of retention elements, each retention element defining retention element apertures. Folding each of the bridge regions into a bridge loop and defining a coaptation neck between each bridge loop and two adjacent leaflets, the bridge loops extending radially away from the tube axis. Disposing a retention element into each of the bridge loops. Suturing each retention element to the respective bridge loop passing suture through the bridge apertures and the retention element apertures that are aligned therewith. Cutting a leaflet frame from a metal tube defining leaflet frame windows and commissure posts therebetween where each commissure post defines a post slot dimensioned to receive a double thickness of the bridge region. Providing leaflet window frame apertures in the leaflet window frame and post apertures in the commissure posts. Disposing each coaptation neck in a respective post slot with the retention elements adjacent the post outer side and disposing the leaflets in the leaflet frame. Aligning the retention element apertures with the post apertures. Suturing each retention element to the respective commissure post passing suture through the retention element apertures and the post apertures that are aligned therewith. Folding the fold-over portions of each leaflet along the leaflet frame inflow edge and against the leaflet frame outer side aligning the fold-over apertures with the leaflet window frame apertures. And suturing each fold-over portion to the respective leaflet window frame passing suture through the fold-over apertures and the leaflet window frame apertures that are aligned therewith.

In accordance with an embodiment the method may further comprise providing strips of fabric, wrapping and sewing the fabric on the leaflet frame to provide a cushion between the leaflet frame and the leaflet construct, and trimming the fabric to approximately 3 mm from the leaflet frame outflow edge of the leaflet frame.

In accordance with an embodiment the method may further comprise cutting a base frame from a metal tube defining base frame apertures, and coupling the base frame to the leaflet frame inflow edge of the leaflet frame.

In accordance with an embodiment the method may further comprise providing a fabric tube and inserting the fabric tube through the base frame along its flow axis. Folding the fabric outflow edge of the fabric over the base frame outflow edge of the base frame. Sewing the fabric into place using suture through the base frame apertures in the base frame. Inverting the fabric inflow edge of the fabric tube over the base frame. Sewing the fabric tube into place using suture through base frame apertures along the inflow edge of the base frame. Disposing a sewing cuff insert inside a pocket defined by the inverted fabric tube and tucking the fabric tube in between the base frame and the sewing cuff insert such that all the slack of the fabric tube is removed around the sewing cuff. Placing the leaflet frame coaxially with and adjacent to the base frame and inside the fabric tube. Trimming the fabric tube approximately 5 mm from the leaflet frame outflow edge and suturing the leaflet frame to the base frame at the leaflet window base using suture passing through the respective leaflet window frame apertures and the base frame apertures. Folding the trimmed edge of the fabric tube over the leaflet frame outflow edge, tucking the trimmed edge underneath itself to conceal any frayed edges, and sewing the fabric tube to the fabric on the leaflet frame.

EXAMPLE

By way of example, one embodiment of a valve was made as follows:

A surgical prosthetic heart valve was constructed in the following manner. A leaflet construct 300, including fold-over apertures 308 and bridge apertures 309, was cut from the leaflet coupon using a CO2 laser according to the pattern shown in FIG. 3.

Three retention elements 400 made from PEEK, shown in FIG. 3, were sewn onto the bridge loop 338 of the bridge region 330 of the leaflet construct 300, as shown in FIGS. 5 and 6. The retention element 400 is provided with retention element apertures 408 that align with bridge apertures 309 on the leaflet construct 300. A partial view of the resulting assembly is shown in FIG. 2.

A leaflet frame 200 and base frame 500 were laser cut, including leaflet frame apertures 208 and base frame apertures 508, respectively, and electropolished from a tube of cobalt chromium (MP35N) with a 25 mm OD and 0.4 mm wall thickness, as shown in FIG. 3. The frames were cleaned in an ultrasonic bath of ethanol to remove contaminants. Three strips of polyester knit fabric were wrapped and sewn on the leaflet frame, to provide a cushion between the leaflet frame 200 and the leaflet construct 300. A post slot 217 of the commissure post 210 large enough (approximately 0.254 mm) to accommodate a double thickness of the leaflet construct 300 at the bridge region 330 was provided. The remaining polyester knit fabric was trimmed off approximately 3 mm from the leaflet frame outflow edge 224 of the leaflet frame 200 shown in FIG. 4. The leaflet construct 300 with retention elements 400 was placed onto the leaflet frame 200 by sliding each coaptation neck 340 in the post slot 217 with the retention elements 400 on the post outer side 212, as shown in FIG. 2. The retention element apertures 408 were aligned with leaflet frame apertures 208 on the leaflet frame 200 and were sewn into place with suture 700, as shown in FIG. 6. The leaflet construct 300 includes fold-over portions 324 and fold-over apertures 308 along attachment edges. The fold-over portions 324 were folded along the leaflet frame inflow edge 220 of the leaflet frame 200 up against the leaflet frame outer side 204 where fold-over apertures 308 in the fold-over portions 324 coincide with leaflet frame apertures 208 of the leaflet frame 200 and were sewn into place with suture 700 as shown in FIG. 7.

A tube of polyester knit fabric about 24 mm in diameter and at least 10 cm in length was inserted through the base frame 500 along its flow axis. The fabric outflow edge of the polyester knit fabric was folded over the base frame outflow edge 524 of the base frame 500 and sewn into place using suture 700 through base frame apertures 508 in the base frame 500 (not shown). The fabric inflow edge of the polyester knit fabric tube was inverted over the base frame 500 and sewn into place using suture 700 through base frame apertures 508 along the base frame inflow edge 520 of the base frame 500. A silicone sewing cuff insert was placed over the base frame 500 and inside of the inverted polyester knit fabric tube. The polyester knit fabric tube was tucked in between the base frame 500 and the sewing cuff insert such that all the slack was removed around the sewing cuff 600.

The leaflet frame assembly 234 comprising the leaflet frame 200, the leaflet construct 300 and retention elements 400 was coaxially placed adjacent the base frame and inside the polyester knit fabric tube. The polyester knit fabric tube was trimmed approximately 5 mm off the leaflet frame outflow edge 224. The leaflet frame 200 was sutured to the base frame 500 at the leaflet window base 225, with three sutures 700 at each of the three leaflet window bases 225 of the leaflet frame 200. The trimmed edge of the polyester knit fabric was folded over the leaflet frame outflow edge 224. The trimmed edge was tucked underneath itself to conceal any frayed edges and sewn to the polyester knit fabric on the leaflet frame.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed:

1. A method of making a prosthetic valve, the method comprising:
    cutting a leaflet construct from a tube of material such that the leaflet construct includes a plurality of leaflets each separated by a bridge region and having fold-over apertures in fold-over portions of each leaflet and bridge apertures in the bridge region;
    folding each of the bridge regions into a bridge loop, each bridge loop of the plurality of leaflets defining coaptation necks between the bridge loop and two adjacent leaflets of the plurality of leaflets;
    locating a retention element in each of the bridge loops;
    suturing each retention element to the respective bridge loop by passing suture through the bridge apertures and respective retention element apertures that are aligned therewith;
    disposing each coaptation neck in a respective post slot of a leaflet frame that is a tube defining leaflet frame windows and a plurality of commissure posts therebetween, where each of the plurality of commissure posts defines a post slot dimensioned to receive a double thickness of the tube at the bridge region and the leaflet frame has leaflet window frame apertures in the leaflet window frame and post apertures in the commissure posts;
    positioning the retention elements adjacent an outer side of a respective one of the commissure posts and disposing the leaflets in the leaflet frame;
    aligning the retention element apertures with the post apertures;
    suturing each retention element to the respective commissure post passing suture through the retention element apertures and the post apertures that are aligned therewith;
    folding the fold-over portions of each leaflet along a leaflet frame inflow edge and against a leaflet frame outer side aligning the fold-over apertures with the leaflet window frame apertures; and
    suturing each fold-over portion to the respective leaflet window frame passing suture through the fold-over apertures and the leaflet window frame apertures that are aligned therewith.

2. The method of claim 1, wherein the tube of material comprises one or more layers of expanded PTFE composite.

3. The method of claim 1, further comprising:
    providing strips of fabric;
    wrapping and sewing the strips of fabric on the leaflet frame to provide a cushion between the leaflet frame and the leaflet construct; and
    trimming the strips of fabric to adjacent a leaflet frame outflow edge of the leaflet frame.

4. The method of claim 3, further comprising:
    providing a base frame that is a tube defining base frame apertures, the base frame defining a base frame central axis;
    placing the leaflet frame and base frame in coaxial alignment; and
    coupling the base frame to the leaflet frame inflow edge of the leaflet frame.

5. The method of claim 4, further comprising:
    providing a fabric tube;
    inserting the fabric tube through the base frame along the base frame central axis;
    folding a fabric outflow edge of the fabric tube over a base frame outflow edge of the base frame;
    coupling the fabric outflow edge to the base frame by sewing the fabric outflow edge using suture through the base frame apertures in the base frame;
    inverting a fabric inflow edge of the fabric tube over the base frame;
    coupling the fabric inflow edge to an inflow edge of the base frame by sewing the fabric inflow edge using suture through the base frame apertures that are adjacent the inflow edge of the base frame;
    disposing a sewing cuff insert inside a pocket defined by the fabric tube that has been inverted;
    tucking the fabric tube in between the base frame and the sewing cuff insert such that all slack of the fabric tube is removed around the sewing cuff insert;
    placing the leaflet frame coaxially with and adjacent to the base frame and inside the fabric tube;
    trimming the fabric tube to adjacent a leaflet frame outflow edge;
    suturing the leaflet frame to the base frame at a leaflet window base using suture passing through the respective leaflet window frame apertures and the base frame apertures;
    folding a trimmed edge of the fabric tube over the leaflet frame outflow edge;
    tucking the trimmed edge underneath itself to conceal any frayed edges; and
    sewing the fabric tube to the strips of fabric on the leaflet frame.

6. A method of making a prosthetic valve, the method comprising:
    forming a leaflet construct including a plurality of leaflets that are contiguous with one another and are interconnected by a plurality of bridge regions;
    folding each of the plurality of bridge regions into a plurality of bridge loops;
    passing each of the plurality of bridge loops through a plurality of post slots in a plurality of commissure posts of a leaflet frame;
    receiving a plurality of retention elements in the plurality of bridge loops such that each of the plurality of retention elements is abutted against an outer side of the plurality of commissure posts of the leaflet frame;

securing the plurality of bridge loops to the plurality of retention elements, the plurality of retention elements to the plurality of commissure posts, and the plurality of bridge loops to the plurality of commissure posts; and folding portions of each of the plurality of leaflets over the leaflet frame to define a plurality of fold-over portions and securing the fold-over portions in a folded configuration to couple the fold-over portions to the leaflet frame.

7. The method of claim 6, further comprising using a plurality of sutures to secure the plurality of bridge loops to the plurality of retention elements, the plurality of retention elements to the plurality of commissure posts, and the plurality of bridge loops to the plurality of commissure posts.

8. The method of claim 6, further comprising using a plurality of sutures to secure the fold-over portions in the folded configuration to couple the fold-over portions to the leaflet frame.

9. The method of claim 6, further comprising forming the leaflet construct including the plurality of leaflets that are contiguous with one another and are interconnected by the plurality of bridge regions by cutting a tube of material into the leaflet construct.

10. The method of claim 6, further comprising forming a plurality of apertures through each of the plurality of bridge regions, each of the plurality of commissure posts, and each of the plurality of retention elements locating a plurality of securement structures in the plurality of apertures through each of the plurality of bridge regions, each of the plurality of commissure posts, and each of the plurality of retention elements to secure the plurality of bridge regions, the plurality of commissure posts, and the plurality of retention elements together.

11. The method of claim 6, wherein the leaflet construct is formed of one or more layers of expanded PTFE composite.

* * * * *